United States Patent
Platt et al.

(10) Patent No.: US 6,905,641 B2
(45) Date of Patent: Jun. 14, 2005

(54) DELIVERY SYSTEM FOR POST-OPERATIVE POWER ADJUSTMENT OF ADJUSTABLE LENS

(75) Inventors: Ben C. Platt, Stevenson Ranch, CA (US); Christian A. Sandstedt, Pasadena, CA (US); James A. Ebel, Glendale, CA (US)

(73) Assignee: Calhoun Vision, Inc., Pasadena, CA (US)

( * ) Notice: Subject to any disclaimer, the term of this patent is extended or adjusted under 35 U.S.C. 154(b) by 394 days.

(21) Appl. No.: 09/964,786

(22) Filed: Sep. 26, 2001

(65) Prior Publication Data

US 2002/0100990 A1 Aug. 1, 2002

Related U.S. Application Data

(60) Provisional application No. 60/235,457, filed on Sep. 26, 2000, provisional application No. 60/234,454, filed on Sep. 26, 2000, and provisional application No. 60/269,151, filed on Feb. 15, 2001.

(51) Int. Cl.[7] .............................................. B29D 11/00
(52) U.S. Cl. ...................... 264/1.38; 264/40.1; 264/409
(58) Field of Search .............................. 264/1.36, 1.38, 264/408, 409, 40.1; 607/141; 351/219; 623/6.11

(56) References Cited

U.S. PATENT DOCUMENTS

| | | | | |
|---|---|---|---|---|
| 4,755,056 A | * | 7/1988 | Yasuda et al. ................. | 356/51 |
| 5,229,797 A | | 7/1993 | Futhey et al. | |
| 5,258,024 A | | 11/1993 | Chavel et al. | |
| 5,432,876 A | * | 7/1995 | Appeldorn et al. ............ | 385/31 |
| 5,549,668 A | * | 8/1996 | O'Donnell, Jr. ........... | 623/6.22 |
| 5,684,636 A | | 11/1997 | Chow et al. | |
| 5,998,096 A | | 12/1999 | Umemoto et al. | |
| 6,086,204 A | | 7/2000 | Magnante | |
| 6,139,147 A | | 10/2000 | Zhang | |
| 6,325,792 B1 | * | 12/2001 | Swinger et al. ................. | 606/4 |
| 6,353,502 B1 | * | 3/2002 | Marchant et al. ........... | 359/626 |
| 6,382,795 B1 | * | 5/2002 | Lai .............................. | 351/212 |
| 6,450,642 B1 | * | 9/2002 | Jethmalani et al. ......... | 351/219 |
| 6,575,572 B2 | * | 6/2003 | Lai et al. ..................... | 351/211 |
| 6,648,473 B2 | * | 11/2003 | DellaVecchia et al. ...... | 351/221 |
| 2003/0048411 A1 | | 3/2003 | Jethmalani et al. | |

OTHER PUBLICATIONS

Brandser, Rennaug, et al., "Accuracy of IOL calculation in cataract surgery," Ophthalmological Journal of the Nordic Countries, vol. 75, No. 2., p. 162–165, (Apr. 1997).

Oshika, Tetsuro, et al. "Three year prospective, randomized evaluation of intraolucar lens implantation through 3.2 and 5.5 mm incisions." J. Cataract Refract Surg, vol. 24, p. 509–514, (Apr.1998).

Liang, Junzhong, et al., "Aberrations and retinal image quality of the normal human eye," J. Opt. Soc. Am. A. vol. 14, No. II, p. 2873–2882, (Nov. 1997).

He, J. C., et al., "Measurement of the wave–front aberration of the eye by a fast pyschophysical procedure," Optical Society of America, vol. 15, No. 9, p. 2449–2456, (Sep. 1998).

(Continued)

Primary Examiner—Chris Fiorilla
Assistant Examiner—Yewebdar Tadesse
(74) Attorney, Agent, or Firm—Fulbright & Jaworski LLP (57) ABSTRACT

A method and instrument to irradiate a light adjustable lens, for example, inside a human eye, with an appropriate amount of radiation in an appropriate intensity pattern by first measuring aberrations in the optical system containing the lens; aligning a source of the modifying radiation so as to impinge the radiation onto the lens in a pattern that will null the aberrations. The quantity of the impinging radiation is controlled by controlling the intensity and duration of the irradiation. The pattern is controlled and monitored while the lens is irradiated.

27 Claims, 8 Drawing Sheets

OTHER PUBLICATIONS

Liang, Junzhong, et al., "Objective measurement of wave aberrations of the human eye with the use of a Hartmann–Shack wave–front sensor," Optical Society of America, vol. 11, No. 7, p. 1949–1957, (Jul. 1994).

Salmon, Thomas O., et al., "Comparison of the eye's wave–front aberration measured psychophysically and with the Shack–Hartmann wave–front sensor," Optical Society of America, vol. 15, No. 9, p. 2457–2465, (Sep. 1998).

Liang, Junzhong, et al., "Supernormal vision and high–resolution retinal imaging through adaptive optics," Optical Society of America, vol. 14, No. 11, p. 2884–2891, (Nov. 1997).

Mahoney, Robert K., et al., "Laser Adjustable Lens: a new generation in implants," Ocular Surgery News, vol. 18, No. 15, (Aug. 1, 2000).

Charters, Lynda, "New IOL lets laser adjust refraction postimplantation," Hotel & Motel Management, Ophthalmology Times, (Jul. 1, 2000).

Bethke, Walter, "An IOL You Can Customize," Review of Ophthalmology, (Sep. 2000).

* cited by examiner

FIG. 8
SPECTRAL OUTPUT OF UV LED

$$I = I_0 \left(1 - \frac{r^2}{r^2_{max}}\right)$$

FIG. 14

$$I = I_0 \left(0.65 \frac{r^2}{r^2_{max}} + 0.35\right)$$

FIG. 15

DELIVERY SYSTEM FOR POST-OPERATIVE POWER ADJUSTMENT OF ADJUSTABLE LENS

CROSS REFERENCE TO RELATED APPLICATIONS

This application is based on U.S. Application Ser. Nos. 60/235,457, filed Sep. 26, 2000; 60/235,454 filed Sep. 26, 2000; and 60/269,151, filed Feb. 15, 2001.

BACKGROUND OF THE INVENTION

1. Field of the Invention

This invention relates generally to the post-manufacture alteration of the properties of an optical device, and, more specifically, to the irradiation of light adjustable lenses.

2. Background Information

Cataract surgery procedures involve making an incision in the anterior lens capsule to remove the cataractous crystalline lens and implanting an intraocular lens (IOL) in its place. In general, there are two types of intraocular lenses. One type replaces the eye's natural lens, usually to replace a cataractous lens. The other type is used to supplement an existing lens and functions as a permanent corrective lens. This type of lens (referred to as a phakic IOL) is implanted in the anterior or posterior chamber to correct refractive errors of the eye. In theory, the power for either type of IOL required for emmetropia (i.e., point focus on the retina from light originating at infinity) can be precisely calculated. The power of the implanted lens is selected based on pre-operative measurements of ocular length and corneal curvature to enable the patient to see without additional corrective measures (e.g., glasses or contact lenses). Unfortunately, due to errors in measurement, and/or variable lens positioning and wound healing, about half of these patients undergoing this procedure will not enjoy optimal vision without correction after surgery (Brandser et al., *Acta Opthalmol Scand* 75:162–165 (1997); Oshika et al., *J Cataract Refract Surg* 24:509–514 (1998). Because the power of such IOLs generally cannot be adjusted once they have been implanted, the patient typically must be resigned to the use of additional corrective lenses such as eyeglasses or contact lenses. Rarely is the implanted lens exchanged for one of more appropriate lens power.

An answer to the foregoing problems is a light adjustable lens, which is an optical device whose refractive properties can be changed after its fabrication and insertion into a human eye. Such a lens is described in detail in International Application Ser. No. PCT/US99/41650, filed on Oct. 13, 1999 and published Jul. 20, 2000, the disclosure of which is incorporated herein by this reference. The light adjustable lens has a refraction modulating composition dispersed in a polymer matrix. One to four weeks after the lens has been implanted into the eye and refractive stabilization has occurred, the preexisting optical aberrations or those induced by the surgical procedure are measured. In order to correct these optical aberrations (e.g. spherical power, astigmatism, prism, etc.), a corresponding amount of radiation is applied to the light adjustable lens, which alters the optical properties of the lens either through changes in its shape, its index of refraction, or both. Following one or several irradiations in which portions of the lens have been exposed to selectively and spatially modify the refractive power, the entire lens is irradiated to "lock in" the modified lens.

The irradiation sources that have enough intensity to modify the refractive properties of an implanted, adjustable intraocular lens in situ are either coherent light sources such as a laser, which can potentially cause permanent damage to the retina by creating high intensities focused to a point on the retina, or high power incoherent sources that have to be attenuated by as much as $\frac{1}{1000}$ in order to avoid damage to the eye. Accordingly, there is a need for an irradiation source to modify an intraocular lens, e.g., in situ after implantation of the lens in the eye.

There is also a need to more accurately modify the lens so as to more closely compensate for remaining aberrations, and a need to assure that locking radiation will irradiate the lens behind the iris in patients where the iris does not fully dilate.

SUMMARY OF THE INVENTION

The present invention provides a method and instrument to irradiate a light adjustable lens inside the human eye with an appropriate amount of radiation and a spatially defined intensity pattern. A similar embodiment of the design described here can also be used to irradiate light adjustable lens material for other applications. For example, the invention can be used as an aberration conjugator in correcting other types of optical systems, e.g.: microscopes; telescopes; camera lenses; ex-vivo, custom ordered intraocular lenses (IOLs); and custom ordered contact lenses; and the like. By accurately irradiating the light adjustable lens to correct the patients' vision after implantation, the patient does not have to wear eyeglasses after surgery. Of course, older patients who have lost the ability to accommodate may want to wear some sort of corrective eyewear for near vision. In accordance with embodiments of this invention, following implantation and waiting the necessary time (1 to 4 weeks) for refractive stabilization to occur, aberrations in the eye are measured before, during, and after irradiation. The irradiation source is precisely aligned to the line of sight (LOS) axis of the eye, the intensity and duration of the irradiation are precisely controlled, and the irradiation intensity pattern is controlled and monitored. There is provided a method and instrument that is easy for doctors to use, and which is patient friendly.

Various forms of correction may be required, such as spherical power, astigmatism, and higher order aberrations (e.g. coma, trefoil, third order spherical, etc.). Different amounts and patterns of irradiation will be required to correct the patients' vision. Thus, in a method and instrument for irradiating a light adjustable lens in an optical system with lens modifying radiation, the present invention provides an improvement comprising: measuring the aberrations of the optical system (e.g. the eye) containing the lens (including preexisting aberrations and those induced by the surgical procedure and wound healing) and aligning the source of the modifying radiation so as to impinge the irradiation onto the lens in a spatially defined intensity pattern that will effectively null the aberrations. Controlling the intensity and duration of the irradiation controls the magnitude of the impinging radiation. The pattern is controlled and monitored while the lens is irradiated.

Specific embodiments of the invention provide energy sources for irradiating light adjustable intraocular lenses. Useful sources of irradiation for modifying the light adjustable lens are pulsed UV lasers and arc lamps; and continuous wave (CW) UV sources such as an arc discharge lamp, CW laser, or CW LED. In one embodiment of the invention, an extended ultraviolet light (UV) source is provided, e.g., UV light emitting diodes (LED) for irradiating the lens. The output characteristics of UV LEDs make this source attractive to the present application since they cannot be focused to a tight spot and are limited in total intensity output. Both of these features provide less potential risk to the ocular structures.

In accordance with another embodiment of the invention, modifying light is generated and projected onto the light adjustable lens in a pattern that compensates for the aberration, for example, one that is opposite in phase to the measured aberrations. In a particular form of this embodiment, a UV vertical-cavity surface-emitting laser (VCSEL) array is used to generate a UV intensity pattern and project it onto the surface of a light adjustable lens. Such an arrangement provides advantages in that the optical system is smaller, lighter, more versatile in generating different irradiation intensity patterns, and less complicated than other UV patterning systems. The optical efficiency is higher than other systems, producing less heat; and the operating lifetime of the source is longer.

In another embodiment of the invention, the pattern of modifying light is obtained by use of an apodizing filter having a predetermined intensity profile. In still other embodiments, a spatial light modulator (SLM) or digital mirror device (DMD) can be used. Such devices have been used in LASIX procedures to modify the original lens, but their use in providing a pattern of modifying light for the refraction modulating component of a light adjustable lens is unique. In any event, the necessary pattern of light generated for the correction of the measured optical aberrations can be obtained by the use of wavefront sensor feedback, for example from a Shack-Hartmann sensor. Such a sensor used in conjunction with a deformable mirror (DM) has been widely used to correct the aberrations of an astronomical telescope. Its use in the present invention is unique.

Once the light adjustable lens is modified to the desired extent, the optical properties of the lens are photolocked by irradiating the entire lens with light of the appropriate wavelength to equally and completely photopolymerize any refraction modulating composition remaining in the in the light adjustable lens, i.e. effectively remove the driving force for refractive change.

In addition, another specific concern in the locking irradiation of a light adjustable intraocular lens is the ability to irradiate the lens behind the iris in patients where the iris does not fully dilate. In accordance with another embodiment of this invention, a gonio lens is used to overcome this problem. The gonio lens was originally developed to view behind or in front of the iris at extremely large angles. It is also used to view portions of the retina that are otherwise obstructed by ocular structure. Its use in the present invention to lock in the refractive modifications of a light adjustable lens is unique.

The foregoing has outlined rather broadly the features and technical advantages of the present invention in order that the detailed description of the invention that follows may be better understood. The foregoing, and additional features and advantages of the invention will be described hereinafter, form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying Figures. It is to be expressly understood, however, that each of the Figures is provided for the purpose of illustration and description only and is not intended as a definition of the limits of the present invention.

DESCRIPTION OF REPRESENTATIVE EMBODIMENTS

Generally, a light adjustable lens comprises a first polymer matrix and a refraction modulating composition dispersed therein. The first polymer matrix forms the optical element framework and is generally responsible for many of its material properties. The refraction modulating composition may be a single compound or a combination of compounds that is capable of stimulus-induced polymerization, preferably photo-polymerization. As used herein, the term "polymerization" refers to a reaction wherein at least one of the components of the refraction modulating composition reacts to form at least one covalent or physical bond with either a like component or with a different component. The identities of the first polymer matrix and the refraction modulating compositions will depend on the end use of the optical element. However, as a general rule, the first polymer matrix and the refraction modulating composition are selected such that the components that comprise the refraction modulating composition are capable of diffusion within the first polymer matrix. Put another way, a loose first polymer matrix will tend to be paired with larger refraction modulating composition components and a tight first polymer matrix will tend to be paired with smaller refraction modulating composition components.

Figure 1:
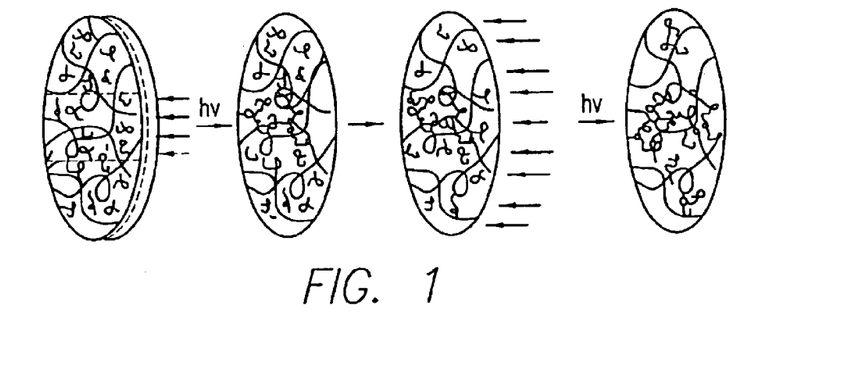
FIG. 1 is a schematic depiction of a lens of the present invention being irradiated in the center followed by irradiation of the entire lens to lock in the modified power.

Upon exposure to an appropriate energy source (e.g., heat or light), the refraction modulating composition typically forms a second polymer matrix in the exposed region of the optical element. The presence of the second polymer matrix changes the material characteristics of this portion of the optical element to modulate its refraction capabilities. After exposure, the refraction modulating composition in the unexposed region will migrate into the exposed region over time causing a swelling reaction or shape change. The amount of refraction modulating composition migration into the exposed region is time dependent and may be precisely controlled. If enough time is permitted, the refraction modulating composition components will re-equilibrate and redistribute throughout the optical element (i.e., the first polymer matrix, including the exposed region). When the region is re-exposed to the energy source, the refraction modulating composition that has since migrated into the region (which may be less than if the refraction modulating composition were allowed to re-equilibrate) polymerizes to further increase the formation of the second polymer matrix. This process (exposure followed by an appropriate time interval to allow for diffusion) may be repeated until the exposed region of the optical element has reached the desired property (e.g., power, refractive index, or shape). At this point, the entire optical element is exposed to the energy source to "lock-in" the desired lens property by polymerizing the remaining refraction modulating composition components that are outside the exposed region before the components can migrate into the exposed region. In other words, because freely diffusable refraction modulating composition components are no longer available, subsequent exposure of the optical element to an energy source cannot further change its power. FIG. 1, taken from International Application Serial No. PCT/US99/41650, supra, illustrates refraction modulation (thus lens power modulation) followed by a lock in.

The irradiation system of the exemplary embodiments consist of several major parts, 1) irradiation source, 2) beam intensity shaper, 3) beam delivery system, 4) method of alignment, 5) calibration element, and 6) diagnostic element, and 7) locking element. Each will be described in more detail below.

Irradiation Source

The irradiation source must be compatible with the photosensitivity of the material being irradiated. In this example, the photopolymer/photoinitiator system is sensitive to UV radiation between the wavelengths of 325 nm and 380 nm so the irradiation source is a UV source. The UV source can be a laser, light emitting diode, or various types of lamps that possess a UV spectrum. The source can also be continuous (CW) or pulsed. The source in this example is a CW mercury arc lamp fitted with an interference filter to produce a beam centered at 365 nm+/−10 nm (Full Width at Full Maximum (FWFM)). Other methods appropriate for use in the present system are described more fully below under the heading: "Method for Irradiating Adjustable Implantable Lenses."

Beam Intensity Shaper

The nature of the beam intensity shaper will depend on the type of radiation used, such as, e-beam, microwave, radio frequency, acoustic, or optical. Optical lenses and apodizing filters will be used in this example since the irradiation source is an arc lamp. The present methods allow a customized pattern of irradiation to generate a customized refraction change in the light adjustable lens. The apodized pattern can be generated using several methods and take different forms. For example, the desired transmission pattern could be a static mask pattern imaged onto photographic film, photochemcially etched onto a substrate using a pattern generating machine, or chrome applied to the appropriate substrate using chemical vapor deposition (CVD). This type of static pattern can be either continuous or half tone structure. In addition, the desired pattern could be dynamic such as that produced by an appropriate spatial light modulator (SLM; e.g. a liquid crystal display (LCD) or a digital mirror device (DMD)), rotating or translating patterns, or any other method to vary the intensity profile or integration time of the exposed radiation dynamically. Some lasers are naturally apodized and may not require further intensity modulation for correcting power or astigmatism in a light adjustable lens. As mentioned in one embodiment, a photographic film mask is used. A photographic film is placed between two glass slides to produce the 3-D intensity profile in a UV projection system similar to a conventional slide projector. The main components are a UV light source, condenser optics, a field lens, an apodizing filter, and projection optics. Methods for generating irradiation profiles are described more fully below under the heading: "Methods for Generating Irradiation Intensity Profiles."

Another potential source for producing a spatially defined, variable intensity pattern is a UV vertical cavity surface-emitting laser (VCSEL). In contrast to the use of static mask or dynamic light modulator (e.g. LCD or DMD) a VCSEL array would only require a laser array, lens matrix array, and projection optics. Thus, the advantages are lower cost and complexity. A controlled VCSEL 2-D array of lasers replaces a mask or SLM, and the light source with its associated condenser optics to irradiate light adjustable lenses or films. The use of a UV vertical cavity surface-emitting laser (VCSEL) constitutes an embodiment of this invention and is described more fully below under the heading "UV-VCSEL UV Pattern Generator."

Beam Delivery System

Figure 2:
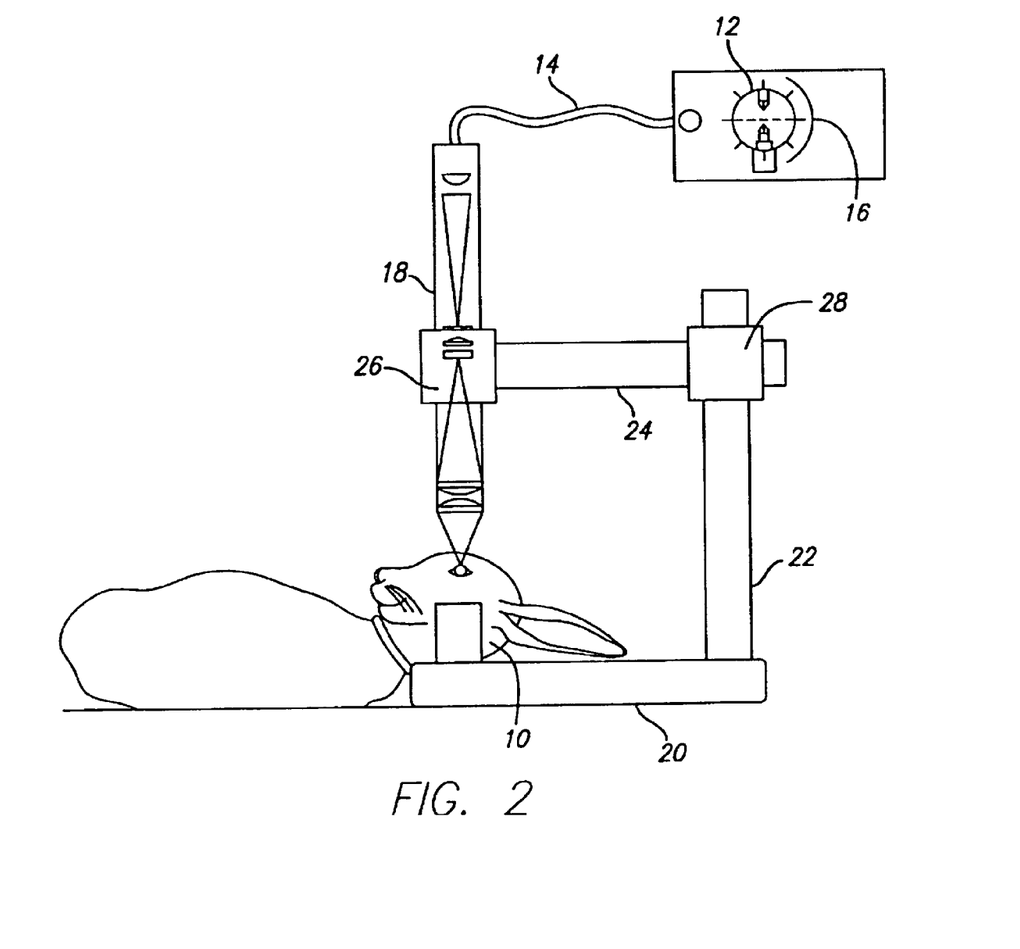
FIG. 2 schematic depiction of an example of an irradiation system without an internal alignment element.
Figure 3:
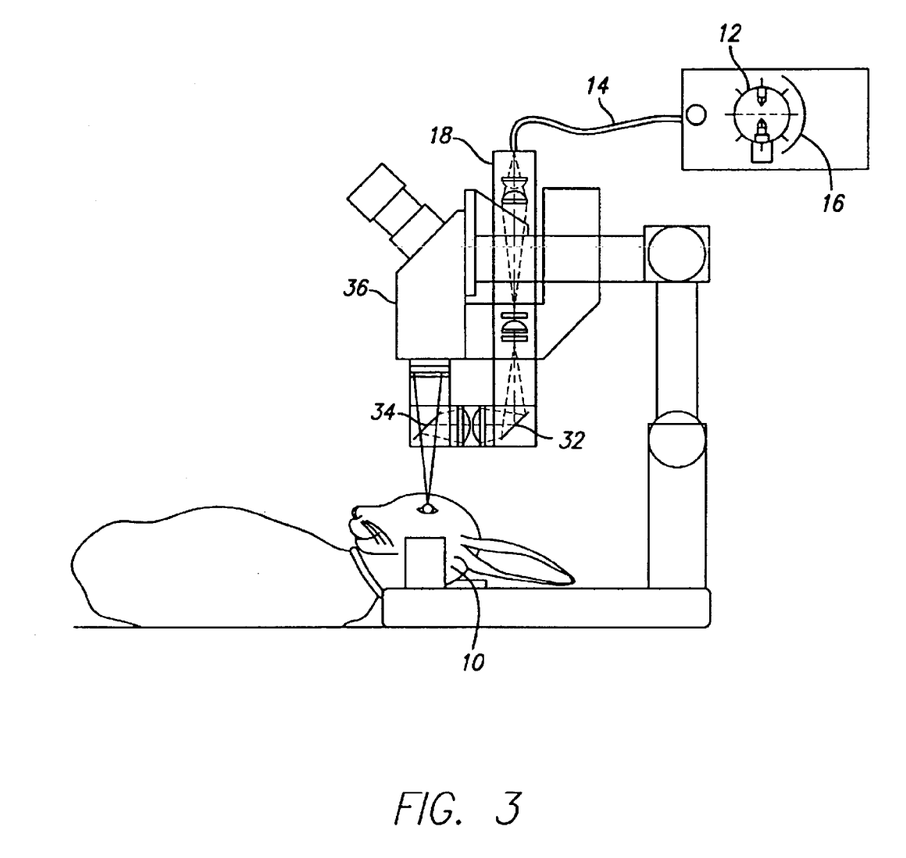
FIG. 3 schematic depiction of an example of irradiation system in a surgical microscope configuration.
Figure 5:
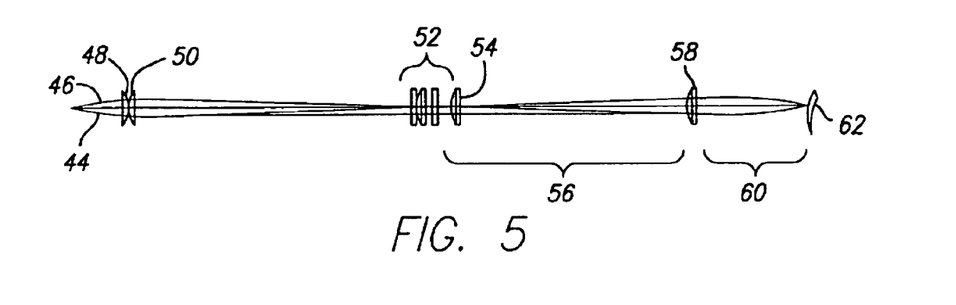
FIG. 5 is a schematic depiction of an example of optical design for imaging through a mask onto light adjustable lens.

The beam delivery system will depend on the type of beam being delivered. In this example, a UV beam is being delivered so UV transmissive optics will be used. The examples shown in FIGS. 2, 3 and 5 are commonly referred to as critical illumination systems. In these examples, the condenser lenses image the output of the integrator (i.e. the light guide) onto the apodizing filter. An interference filter is placed in the optical train to filter the light to the desired wavelength. The field lens is used to redirect the chief ray of the optical system to minimize light loss from the integrator. The objective lenses image the apodizing filter (intensity pattern) onto the light adjustable lens. Another form of illumination is called Kohler illumination, where the source (the output aperture of the light guide) is imaged onto the objective lens and there is no field lens. Either type of illumination design can be used. In another embodiment of the projection system, the condensing lenses can be removed from the optical setup and an appropriate diffusing element (e.g. a holographic diffusing element) is placed adjacent to the apodizing filter to provide a uniform filed (i.e. a flat top beam intensity profile) impinging on the mask. The projection optics then image the apodizing filter onto the light adjustable lens as with the other above described projection systems.

Method of Alignment

An example of an irradiation system without an internal alignment element is shown in FIG. 2 as used on the eye of a rabbit 10. The light output from an arc lamp 12 is launched into the integrator (in this case an optical fiber in the form of a hollow liquid filled waveguide 14) by a spherical reflector 16. The output of the integrator produces a uniform field. (i.e. a flat top intensity profile). The flat top output of the light guide is focused onto an optical mask generator contained in a tube 18 to produce the desired irradiation pattern. In this illustration, the rabbit's head is secured to a platform 20 having a stand 22. The optics tube 18 is connected to an arm 24 by means of a fine adjustment clamp 26, the arm 24 extending from and secured to the stand 22 by a coarse adjustment clamp 28. The desired irradiation/mask pattern will depend on the desired refractive change in the light adjustable lens and the interaction of the material with the radiation. This relationship will be a mathematical description that we refer to as a nomogram.

The method of alignment includes accurate placement of the irradiation pattern on the light adjustable lens. In this case the light adjustable lens is an intraocular lens implanted in the eye. The two most likely positions of the human patient or other subject is lying down on a table, as shown by the reclining rabbit 10 in FIG. 3, or sitting in a chair, as shown by the human patient 30 FIG. 4. Referring to FIG. 3, UV light from the source fiber 14 directed through the optical mask generator tube 18 is diverted by a mirror 32 to a beam splitter 34 and from there to the rabbit's eye. The beam splitter 34 permits observation of the rabbit's implanted light adjustable lens and of the procedure through a surgical microscope 36 vertically aligned with the beam-splitter 34.

Figure 4:
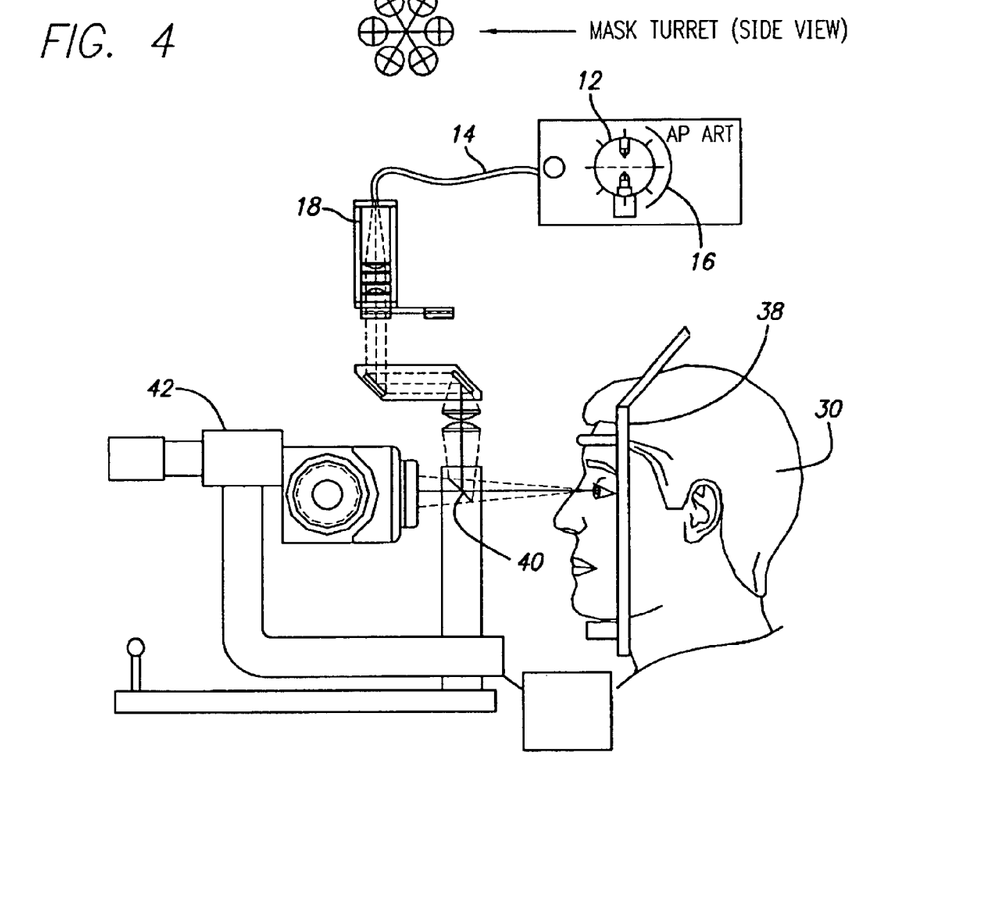
FIG. 4 schematic depiction of an example of an irradiation system in a slit lamp configuration.

Referring to FIG. 4, if the patient is sitting in a chair, his or her head is placed on a headrest 38 that supports the chin and forehead. UV light from the source fiber 14 directed through the optical mask generator tube 18 is diverted by a beam splitter 40 and from there to the patient's eye. The beam splitter 40 is operated in conjunction with an ophthalmic slit lamp 42 that has its own observation optics (not shown) and which allows aligning the irradiation source to the patient.

The slit lamp can have any of a number of configurations, including, hand held, portable, and table mounted. All are applicable to a certain extent. If the patient is lying on a table, a configuration similar to the surgical microscope 36 of FIG. 3 is an appropriate setup.

Once the head is held stable, a video camera or visual microscope co-aligned and parfocal with the optical axis of the irradiation source, is used to align the projected mask/intensity pattern to the light adjustable lens. Internal or external light sources reflecting off the cornea or light adjustable lens can be used as angular alignment aids to align the irradiation source to the light adjustable lens. The reflections may be visible with the video camera, the visual microscope, or another sensor.

In order to compensate for any movements of the patient's eye during the irradiation treatment, a fixation light in the form of a laser point source in the 700–800 nm range is provided for the patient to look at. This will ensure that the aberrations measured prior to treatment and dose delivered to the light adjustable lens is along the patient's visual axis or line of sight (LOS).

Calibration Element

A calibration element is a sensor that monitors the power and/or the intensity profile of the irradiation beam. A beamsplitter is used to provide a sample of the beam for measurement. For simple aberrations, such as optical power or astigmatism, the intensity profile may be fixed with a given mask/pattern generator and it will only be necessary to measure the total power and time of exposure. For customized intensity profiles, it will be necessary to monitor the projected intensity profile and time of exposure. For UV radiation, a UV CCD camera can be used to monitor the intensity.

An example of the optics in the tube 18 of FIGS. 2 to 4 for imaging the mask onto the light adjustable lens is the illumination optical design of FIG. 5. UV light 44 from a source 46, e.g., a liquid filled optical wave guide, is directed through silica optics composed of a PLCX-25.4-38.6-UV lens 48 spaced 1 mm from a PLCX-25.4-30.9-UV lens 50 which is separated, 215 mm in this example, from a compound PLCX-25.4-46.4-UV lens set 52. The UV light 44 passes through a mask 54, then after a variable space 56 through a lightpath gradium CPX-25-60 lens 58, to the light adjustable lens 60 over a variable space 62.

Diagnostic Element

The diagnostic element described here is used to measure the aberrations in the light adjustable lens before, during, and/or after irradiation. There are many instruments available to measure aberrations in the eye. The same instruments used to determine a patient's prescription for eyeglasses can be used to measure optical power and astigmatism errors in the light adjustable lens. There are several instruments for measuring optical power and astigmatism as well as higher order aberrations of the eye. The three most common wavefront sensors used today are based on the Schemer disk, the Shack Hartmann wavefront sensor, and the Talbot interferometer. The application of a wavefront sensor to a light adjustable lens is discussed more fully below under the heading: "Application of Wavefront Sensor to Lenses Capable of Post-Fabrication Power Modification". The diagnostic instrument can be a stand-alone instrument or it can be built into the irradiation system. The diagnostics can be performed during irradiation more readily when the diagnostics are built into the irradiation system.

In a particular implementation: a) a Shack Hartmann wavefront sensor is used to measure the aberrations in the eye; b) a nomogram of the light adjustable lens's response to irradiation is then consulted to determine the required intensity profile to correct the measured aberrations; c) the required intensity profile is placed on a programmable mask generator (such as a digital mirror device); d) a calibration camera is used in a closed loop operation to correct the digital mirror device to compensate for aberrations in the projection optics and non-uniformity in the light source; e) the light adjustable lens is radiated for the prescribed time period; and f) after a specified time, the aberrations in the eye are re-measured to ensure that the proper correction was made. If necessary, the process is repeated until the correction is within acceptable dioptric limits.

Figure 6:
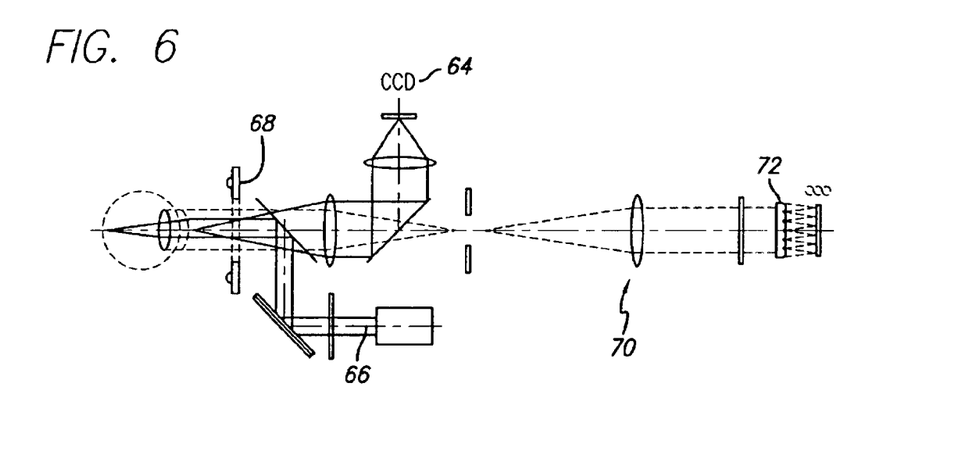
FIG. 6 is a schematic depiction of an embodiment of the Shack-Hartmann wavefront sensor.
Figure 7A:
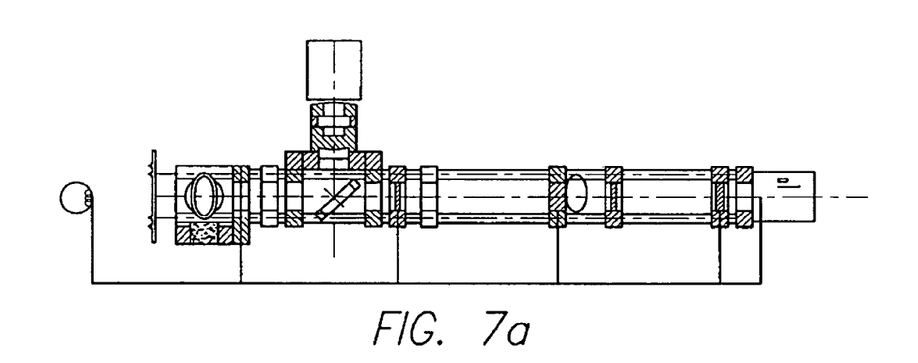
FIGS. 7a and 7b are, respectively, schematic depictions of a side and top view of a Shack-Hartmann wavefront sensor.
Figure 7B:
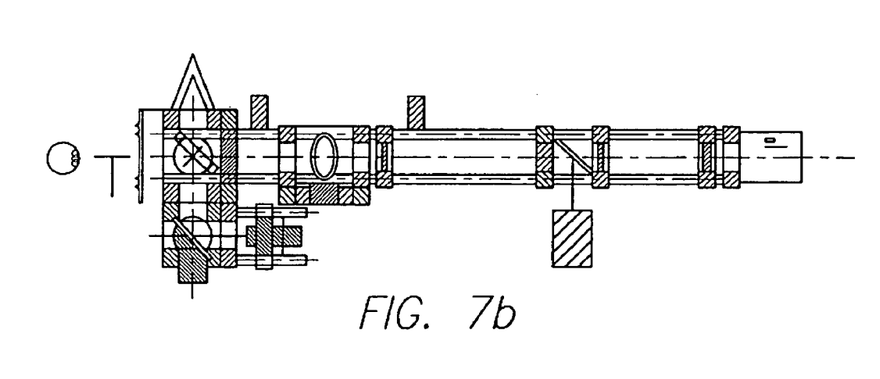

An exemplary embodiment using a Shack-Hartmann wavefront sensor is shown schematically in FIG. 6. Additional detail for the wavefront sensor is shown in the side and top views of FIGS. 7a and 8b. This pair of figures gives some of the dimensions for this exemplary embodiment as shown from the side and top the Shack-Hartmann wavefront sensor.

In the view shown in FIG. 6, for convenience of illustration, the CCD imaging path is drawn to the side of the system. In reality, the CCD camera 64 is mounted on top of the system. The collimated laser beam 66, wavelength 780 nm is focused on the retina. The CCD camera 64 and a red fixation light 68 provides the surgeon with the ability to align the Shack-Hartmann wavefront sensor 70 to the LOS of the patient. The image can be focused by moving the sensor back and forth relative to the eye, which ensures that the wavefront sensor is imaged at the output pupil of the patient's eye The laser light 66 is reflected off the retina and the exiting wavefront contains information regarding the aberrations of the eye. The theory of using a Shack-Hartmann wavefront sensor to measure the aberrations of the human eye is well documented in the literature so that only a brief description will be given here. The lenslet array 72 divides the wavefront reflected off the retina into a number of subapertures and then measures the tilt in the wavefront relative to an ideal, "aberrationless" wavefront. The measured slope is then used to reconstruct the aberrated wavefront whereby it is fit to a set of Zernike polynomials whose individual orders represent a particular optical aberration and their corresponding coefficients represent the magnitude of the aberrations in dioptric error. The severity of each of these components may then be analyzed and corrected through the techniques of this invention.

Locking Element

Once the aberrations are corrected, locking irradiation is applied. The locking irradiation may or may not be applied with the same irradiation system. In those cases where the iris does not fully dilate, it may be necessary to irradiate the light adjustable lens behind the iris. In accordance with another embodiment of the invention a gonio lens is used for this purpose as will be more fully described below under the heading "Gonio Lens to Lock Light Adjustable Lens."

The following will provide additional detail of various embodiments.

Method for Irradiating Adjustable Implantable Lenses

One form of energy used to irradiate an optical element e.g., a light adjustable lens is UV irradiation in the range 320–400 nm. For example, a Helium Cadmium (HeCd) laser operating at 325 nm and a mercury (Hg) arc lamp spectrally filtered for the emission lines at 334 and 365 nm have been used in this invention. These UV sources, including the tripled frequency laser diode pumped solid state YAG laser operating at 355 nm, an argon ion laser operating in the 350–360 nm range, a deuterium discharge lamp, and broad band xenon:mercury lamps operating with any narrow band spectral filter are useful sources for conducting UV irradiation tests on light adjustable materials and lenses.

There are potential safety issues related to each of these sources. When using a coherent source such as a laser there is the potential that the source can be focused to a point on the retina, creating high intensities that can cause permanent damage. Extended, incoherent sources such as arc lamps are attractive from the standpoint that they cannot be focused to a tight spot; however, these sources do possess enough output irradiance that they must be attenuated by as much as $\frac{1}{1000}$ for use in irradiating the light adjustable lenses. Thus, improper use of the lamp, mechanical, or electrical failure could result in applying high intensities to the ocular structures and subsequent damage.

A safer source would be one that cannot be focused to a point and has only enough power to expose/irradiate the intraocular lens material. While in its broader aspects, irradiation yielding an intensity of 0.1 to 100 $mW/cm^2$ can be used, in accordance with an embodiment of the invention, 0.6 to 0.8 milliwatts (mW) of total UV power, in the 350 to 380 nm wavelength range are sufficient to create the desired power change. With optical and corneal transmission losses, the total required power of the UV source in this embodiment will be approximately 2.5 to 3.5 mW. For a 6.0 mm diameter lens, the power source would be irradiating at an intensity of 9.75 to 12.25 $mW/cm^2$.

Figure 8:
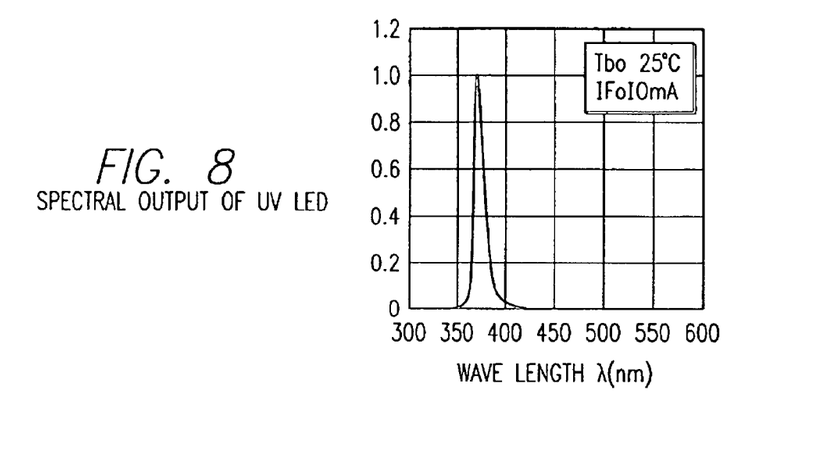
FIG. 8 illustrates a spectral output of a UV Light Emitting Diode.
Figure 9A:
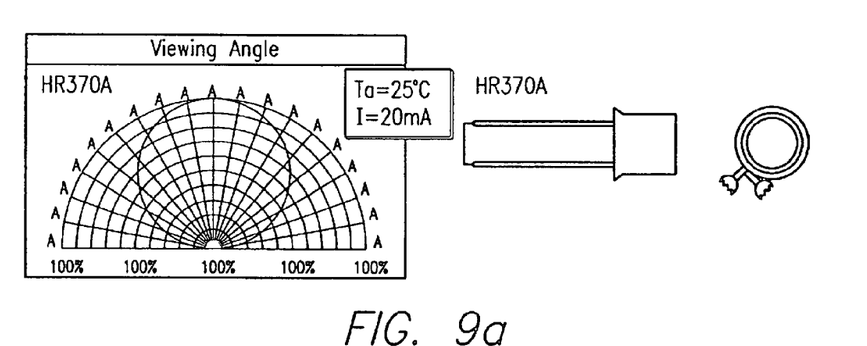
FIGS. 9a and 9b show mechanical descriptions and irradiation patterns of a UV Light Emitting Diode.
Figure 9B:
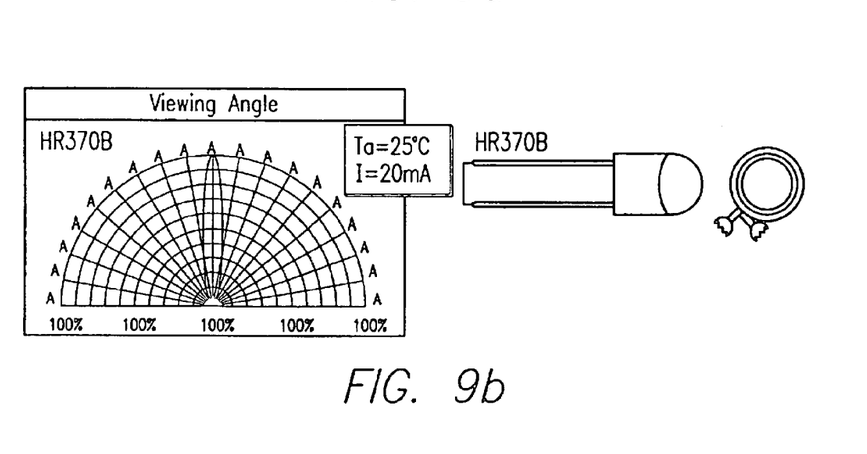

In accordance with the present invention, a UV LED can be a suitable energy source for irradiation of the light adjustable lens. For example, one can use a UV LED available on the market that has an optical output power of 0.75 to 1 mW centered at 370 nm with a full width half max spectral bandwidth of +/−10 nm. The commercially available UV LED is an extended source and it can be focused to a small enough size to couple into a liquid filled optical fiber. The spectral output is shown in FIG. 8. A description of the mechanical package and radiation profiles from the UV LEDs is shown in FIGS. 9a and 9b. Optical and electrical properties of the UV LED, obtained from a vendor (Sander Electronics) specification sheet are given in Table 1.

TABLE I

Absolute Maximum Ratings (Ta = 25° C.)

| | Symbol | Unit | HR370A | HR370B | |
|---|---|---|---|---|---|
| DC Forward Current | IF | MA | 15 | 15 | |
| Pulse Forward Current | IFP | MA | 30 | 30 | 1) |
| Reverse Voltage | VR | V | 5 | 5 | |
| Power Dissipation | PD | MW | 45 | 45 | |
| Operating temperature | Topt | ° C. | −30 . . . +80 | −30 . . . +80 | |
| Storage Temperature | Tstg | ° C. | −40 . . . +100 | −40 . . . +100 | |

HR370A
Electrical Optical Characteristics (Ta = 25° C.)

| | Symbol | Unit | Condition | Min. | Typ. | Max. |
|---|---|---|---|---|---|---|
| DC Forward Voltage | VF | V | IF = 10 mA | — | 3,9 | — |
| DC Reverse Current | IR | MA | VR = 5 V | — | — | 50 |
| Optical Power Output | PO | MW | IF = 10 mA | — | 1000 | — |
| Peak Wavelength | Λ | Nm | IF = 10 mA | — | 370 | — |
| Spectrum Half Width | Δλ | Nm | IF = 10 mA | — | 12 | — |

HR370B
Electrical Optical Characteristics (Ta = 25° C.)

| | Symbol | Unit | Condition | Min. | Typ. | Max. |
|---|---|---|---|---|---|---|
| DC Forward Voltage | VF | V | IF = 10 mA | — | 3,9 | — |
| DC Reverse Current | IR | MA | VR = 5 V | — | — | 50 |
| Optical Power Output | PO | MW | IF = 10 mA | — | 750 | — |

TABLE I-continued

| Peak Wavelength | λ | Nm | IF = 10 mA | — | 370 | — |
|---|---|---|---|---|---|---|
| Spectrum Half Width | Δλ | Nm | IF = 10 mA | — | 12 | — |

1) Pulse width max. 10 ms, Duty ratio max. 1/10

In one embodiment, 2 to 10 UV LEDs are coupled into a 5 mm diameter optical fiber. In another embodiment, 4 to 8 UV LEDs are coupled into a 5 mm diameter optical fiber. UV LEDs can be added or subtracted as required to produce a safe and sufficient power level at the light adjustable lens implanted in the eye.

In a particular example, the light adjustable lens is implanted in a patient's eye and the eye's refraction post operatively is allowed to stabilize. Aberration analysis is made of the patient's eye using standard refraction techniques and/or a wavefront sensor. Using the knowledge of the eye's measured aberrations in conjunction with the previously derived nomogram permits calculation of the desired irradiation profile and dosage to correct the patient's vision by correcting the light adjustable lens using the UV LED as the light source.

The UV LED is a suitable safe light source to use in the irradiation system for modifying the optical properties of light adjustable lens in patients. It has limited brightness and limited size. The maximum possible irradiance will be kept below the American National Standards Institute (ANSI) guidelines, and the minimum size of the spot on the light adjustable lens will be the image of the output of the optical fiber.

Methods for Generating Irradiation Intensity Profiles

Depending upon the light adjustable lens formulation, exposure to the appropriate frequency of light will cause refraction modulation composition to diffuse into the irradiated volume, producing a concomitant change in refractive power of the lens (FIG. 1). The majority of the change in power of the light adjustable lens is due to swelling or shrinkage in the affected region. Although, it is possible that some localized change in refractive index could occur as well since the refractive index of a closed thermodynamic system such as a light adjustable lens is proportional to the number of particles per volume. For example, if the lens is irradiated with a profile as that shown in FIG. 14 then molecules in the irradiated region will polymerize producing a difference in chemical potential between the irradiated and unirradiated regions effectively setting up a diffusion gradient between the irradiated and unirradiated regions. To reestablish thermodynamic equilibrium, the refraction modulating composition in the unexposed region will diffuse towards the center producing localized swelling and an increase in lens power. If the lens is irradiated with a pattern as that shown in FIG. 15 then molecules will diffuse out from the central part of the lens producing an effective decrease in lens power in the center of the lens. This swelling is not necessarily a linear function of the irradiation because of boundary conditions at the edge of the lens, non-uniform thickness across the lens, and, possibly, non-linear response of the lens material to the irradiation. The irradiation profile, amplitude, and exposure time must be tailored for each patient to produce the correct amount of change in the IOL. This includes IOL power change, astigmatism, spherical aberrations, and other irregularities. This is referred to as customized irradiation.

According to an embodiment of the present invention, a spatial light modulator can be used to generate a customized irradiation intensity profile for a composition comprising a refraction modulating composition dispersed in a polymer matrix forming a lens, e.g., an IOL. The spatial light modulator can be any suitable ones known to one skilled in the art. In one embodiment, the spatial light modulator is a liquid crystal display or a digital light processor.

For example, electromagnetic irradiation in the UV, visible, or near infrared portions of the spectrum is easily projected onto the lens by using a projection system similar to the ones used in commercial video/computer projection systems. Nevertheless, these projectors use the liquid crystal display or digital light processor to replace the film used in the projectors. Liquid crystal displays can operate in either transmission or reflection mode. Since they rotate the plane of polarization of the light, polarized light and an analyzer must be incorporated into the optical system.

Digital light processors are composed of an array of tiny square mirrors typically 17 microns on a side. Rather than modulate the intensity of the beam, they modulate the time the beam is on the screen. The tiny mirrors tilt +/−10 degrees at a rate of 60 kHz. If the mirror is activated to the on position, the light striking the mirror is reflected into the projection lens. If the mirror is not in the on position, the light reflects to a beam dump and does not make it to the screen. For each of the 60 kHz frames, each mirror is either ON or OFF. Thus, the mirror activation is binary. For uniform illumination on the digital light processor, the energy density profile applied to the lens is proportional to the number of times each mirror is activated and not to the intensity of the beam.

The method of using constant incident intensity and spatially varying the exposure time has several advantages: a) it avoids trying to produce exposure levels below the intensity threshold level (the minimum irradiation level that any effect occurs), b) it avoids having to compensate for the material efficiency versus intensity level, and c) it makes the nomograms (a plot detailing an IOLs response to light intensity, profile, and duration) much easier to develop.

Figure 10A:
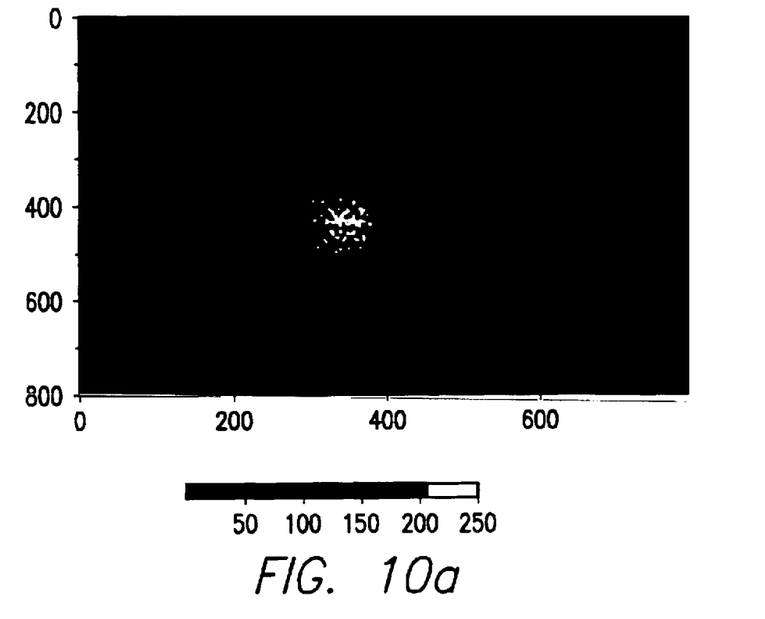
FIGS. 10a and 10b are examples of irradiation profiles for correcting the optical power of a light adjustable lens.
Figure 10B:
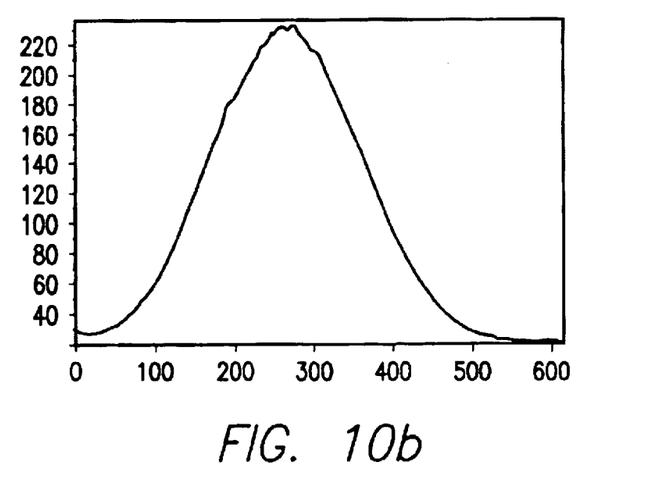

In another embodiment, photographic plates or films are used in a conventional film projection type of system to project an irradiation pattern onto the IOL. As an example, FIG. 10b shows the beam profile of the 365 nm line from a mercury arc lamp after projection of the output of an optical fiber through an apodizing mask (FIG. 10a) possessing a $$1 - \frac{r^2}{r_{max}^2}$$

optical density profile. According to this embodiment, such an intensity profile is used for irradiation of light adjustable lenses and produces desirable optical power changes in the lenses. Each different intensity profile needs a new, individual mask to be placed in the projection system.

By using a liquid crystal display or a digital light processor to generate customized irradiation intensity profiles, the time and expense of making a customized photographic mask can be eliminated. Each customized irradiation intensity profile can be generated on a computer screen and then transferred to the liquid crystal display or digital light processor projector. The variable pattern on the computer screen can be produced with an equation representing a 3-D image of the intensity pattern. The parameters of the equation can be varied by the user or the physician, using the patient's refraction and a nomogram. The physician can also make adjustments to the pattern/equation based on his/her own experience. In one embodiment, one can use the patient's refraction plus a wavefront analysis system to calculate the shape of the irradiation intensity profile for customized irradiation of the IOL.

As an example, the procedure in this embodiment generally involves making an incision in the anterior lens capsule to remove the cataractous crystalline lens and implanting a light adjustable lens in its place. After wound healing and subsequent refractive stabilization, the aberrations of the eye are measured either by conventional refraction techniques (defocus and astigmatism), by wavefront analysis (defocus, astigmatism, coma, spherical, and other higher order aberrations), and/or corneal topographical maps (for higher order aberrations). Knowledge of the aberrations as well as their spatial distribution in the eye after post-surgical healing allows the patient's vision to be corrected by a nomogram representing the light adjustable lens' response to light of a particular wavelength, intensity profile, and duration. After determination of the type, magnitude, and spatial distribution of the aberrations in the eye, this information is fed into a computer program that works in conjunction with the nomogram that outputs the correct intensity profile for the as well as the duration of the light. The information of the required intensity profile is then fed into the digital light processor to control the individual mirrors that ultimately determine the output of the digital light processor/projection system and the pattern is projected onto the light adjustable lens. Once the light adjustable lens is irradiated and diffusion of refraction modulating composition to the exposed region has occurred, the eye is again refracted. If further modification of the light adjustable lens is required the sequence of using the nomogram and the digital light processor pattern generator is repeated. Once the desired aberrations have been corrected the entire lens is irradiated to photolock the lens, effectively prohibiting further diffusion and subsequent refractive changes in the light adjustable lens.

In another embodiment, a digital light processor is used for the purpose of generating an irradiation profile/mask for UV irradiation of a light adjustable lens. A commercial digital light processor projector (such as sold by Infocus, Inc., can be purchased, the optics and light source can be removed, and replaced with a UV light source and lens system. The optics and light source can be replaced to irradiate test IOLs. Script can be generated for MatLab (commercial computer program for solving math problems and generating graphic images) or other graphics programs to view 3-D intensity profiles and 2-D intensity projections of those profiles. The computer can then be connected to the modified commercial projector and test IOLs can be irradiated with the calculated profiles. Flat disks and lenses can be made from the light adjustable lens material and irradiated with various patterns, intensity levels, and exposure times to generate one or more irradiation nomograms. Typical intensity patterns can resemble ( )

$$1 - \frac{r^2}{r_{\max}^2} \text{ or}$$

Gaussian profiles (where r is the radius of the optical zone on the IOL). Typical intensity levels range from 2 to 10 mW/cm2 and typical exposure times range from 10 to 60 seconds. Patient's refraction data can be used with the nomogram for correcting the optical power and astigmatism in the IOL. For higher order aberrations, such as spherical aberrations and coma, a wavefront sensor will be required. Although more time consuming, standard refraction techniques have and can be used to measure spherical aberrations.

Examples of Nomograms

Figure 13:
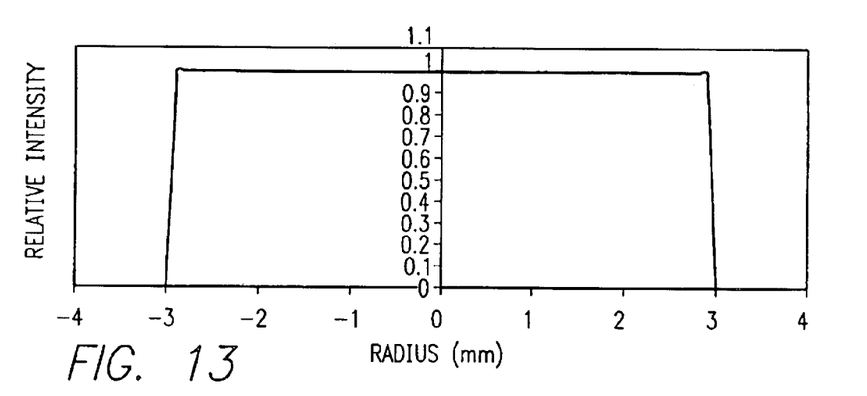
FIG. 13 is a nomogram used in this invention, having a "top hat" intensity profile.
Figure 14:
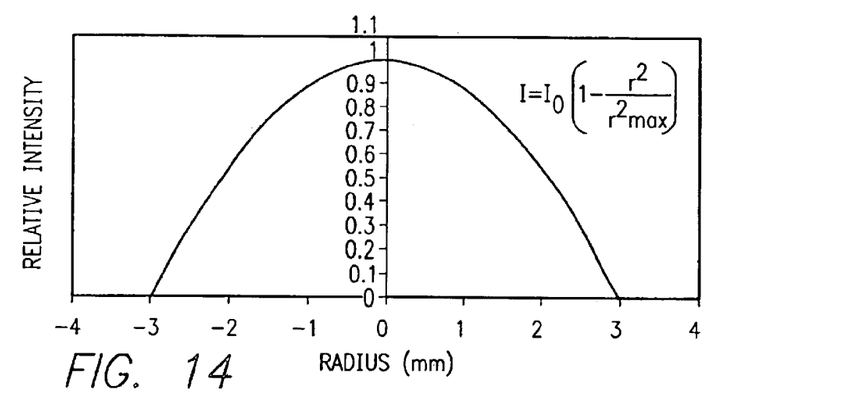
FIG. 14 is another nomogram used in this invention.

An example of this locking irradiation is a "top hat" intensity profile (FIG. 13). The obvious feature of this type of profile is that an even amount of intensity is applied to the lens. As a further example the photolocking intensity (I) profile may be one corresponding to the equation $$I = I_0 \left(1 - \frac{r^2}{r_{\max}^2}\right)$$

as shown in FIG. 14, where $I_0$ is the peak intensity of the beam, r is the radius across the lens, and $r_{max}$ is radius of the image beam on the lens. Such a profile is useful for cases when a UV absorbing additive is placed in the light adjustable lens to protect the retina. Because the light adjustable lens possesses a variable thickness across its diameter the addition of a UV absorbing species to the light adjustable lens can prevent locking irradiation from reaching the back of the lens. Such a situation would cause refraction modulating composition to diffuse from the back of the light adjustable lens towards the front of the light adjustable lens. This action has the affect of flattening the back surface effectively changing the power of the lens. By placing a $$I = I_0 \left(1 - \frac{r^2}{r_{\max}^2}\right)$$

profile down onto the light adjustable lens surface with sufficient intensity to completely penetrate the central thickest part of the light adjustable lens as well as the thinner edges photolocking will be possible.

A treatment nomogram, in its simplest form, represents a xy plot of dioptric power change plotted vs irradiation dose. The response table developed to satisfy these requirements is a nomogram. For simple power correction, the nomogram may simply be a curve on an x, y plot. As an example of a treatment nomogram, 24 light adjustable lenses (nominal power of +20 D) composed of 70 wt % cross-linked silicone matrix, 30 wt % methacrylate endcapped dimethylsiloxane refraction modulating composition, and 1 wt % photoinitiator (For further details regarding the light adjustable lens compositions consult PCT/US99/41650). The first set of 8 lenses were irradiated with 10 mW/cm$^2$ for one 30 second interval using the projection system show in FIG. 5, and beam intensity profile shown in FIG. 15. The second and third sets of 8 light adjustable lenses were irradiated using the same projection system, intensity profile, and intensity conditions as the first set of 8 except that the second set was irradiated with two 30 second exposures separated by 5 seconds, and the third set was irradiated with three 30 second exposures separated by 5 seconds. Twenty four hours post-irradiation, the light adjustable lens system had reached thermodynamic equlibrium as evidenced by stabilization in the power change of the light adjustable lens. The results of these experiments are shown in table 1.

TABLE 1

Figure 15:
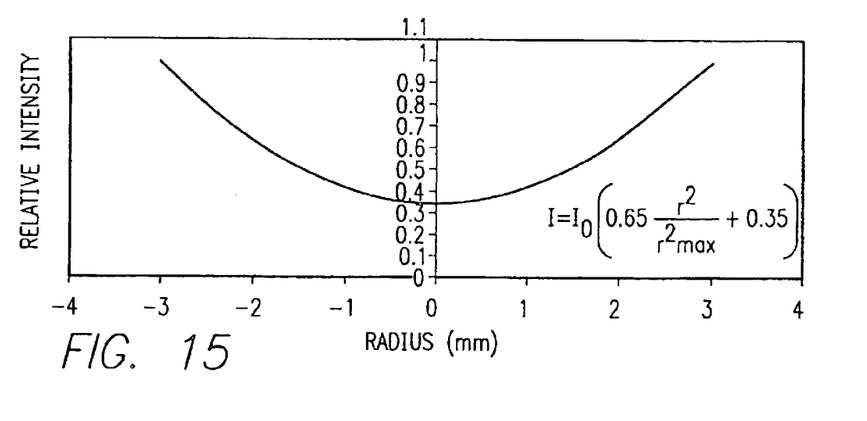
FIG. 15 is still another nomogram used in this invention, having a "top hat" intensity profile.

| Intensity (mW/cm$^2$) | Irradiation Time (seconds) | Intensity Pattern | ΔD 24 Hrs Post Irradiation (Diopters) |
|---|---|---|---|
| 10 | 1 × 30 | FIG. 15 | −0.66 ± 0.02 |
| 10 | 2 × 30 | FIG. 15 | −1.82 ± 0.08 |
| 10 | 3 × 30 | FIG. 15 | −2.65 ± 0.13 |
| 5 | 2 × 30 | FIG. 14 | +1.04 ± 0.15 |

As an example of a positive power change, 8 light adjustable lenses (nominal +20 D power) fabricated with the same composition as the lenes described above. These eight light adjustable lenses were exposed to 5 mW/cm$^2$ using two 30 second doses separated by 5 seconds and the intensity pattern shown in FIG. 14. The results of these experiments and final power change after 24 hours are listed in table 1.

UV-VCSEL Pattern Generator

VCSELs can be single element lasers, 1-D arrays, or 2-d arrays. Each laser element emits a nearly square laser beam from the top surface in a narrow cone of light. Most of the research on these devices has been in the near IR for telecommunication applications. Some visible arrays have been developed for scanning and detecting images. The fill factor for 2-d arrays is usually small because of the space needed for the leads. Lens arrays can be placed on top of the VCSEL arrays to obtain fill factors greater than 90%. These lasers have very high modulation frequencies. If it is too difficult to control the intensity of the lasers, the energy in the exposure can be controlled with pulse width modulation or other modulation methods. By spatially controlling the intensity or average energy in each laser, one can produce an effective beam intensity profile. This pattern/profile is then imaged onto the light adjustable lens or film to produce the desired refraction pattern. The advantage is direct and instantaneous or nearly instantaneous control of the irradiation pattern and increased pattern combinations.

Since the same beam profile variation can be accomplished with various types of spatial light modulators and standard display or projection optics, the ramifications the UV-VCSEL of this embodiment are in the simplicity and size of the packaging issues are more important when the irradiation system is combined with the wavefront sensor and some type of viewing and video capability.

VCSELs have been used (at other wavelengths) in imaging and scanning applications but not for irradiating light adjustable lenses or films. Such UV-VCSEL arrays are as described in Photomiss Spectra, March 2001, p. 30, incorporated herein by reference.

Figure 11:
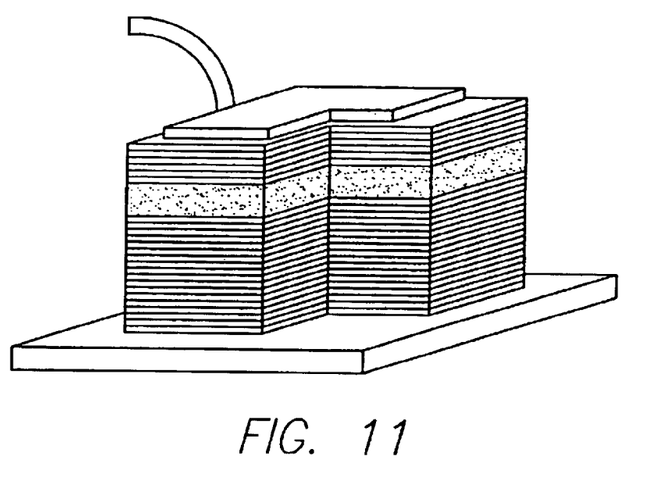
FIG. 11 is a schematic of a vertical cavity surface emitting laser usable in the present invention.

Referring to FIG. 11, in a VCSEL light propagates vertically rather than laterally through the structure. With this orientation the laser cavity can be grown to match the wavelength of laser light. With such a small cavity, the gain bandwidth of the device can only support a single longitudinal mode. In this particular VCSEL, an oxide layer was grown directly above and below the laser cavity to provide both gain and index guiding to the device.

Gonio Lens to Lock Light Adjustable Lens

In accordance with an embodiment of this invention, a gonio lens is used to lock the light adjustable lens by irradiating portions of the light adjustable lens that are blocked by the iris. The advantage of this embodiment is that it can easily deliver radiation at large angles to reach portions of the lens that are blocked behind the iris.

The gonio lens is typically a block of glass that has a radius on one end that closely matches the radius of curvature of the eye. A gel or viscoelastic material is used as an index matching fluid to remove or greatly reduce the optical power of the cornea. A lens on the other end allows one to look directly at the retina. Faceted mirrors are polished on the side of the block of glass that allows one to view the sides of the eye, either above or below the iris. Separate lenses are placed above the facets for focusing lasers inside the eye or aiding in the focus of other optical instruments. Since the areas of the eye are missed between the facets and where the facets come together, the gonio lens is rotated to provide complete coverage. The same missing areas will occur in this application of the gonio lens. Thus, the gonio lens will have to be rotated to provide complete coverage of the locking irradiation behind the iris.

Figure 12:
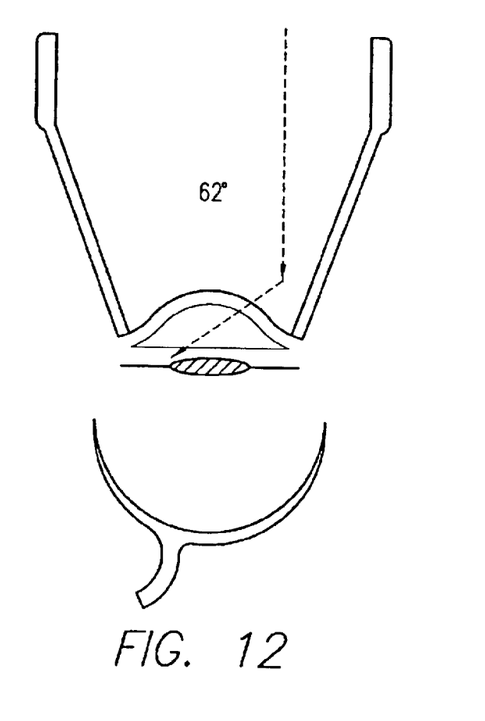
FIG. 12 is gonio lens usable in the present invention.

Gonio lenses come with 1 to 4 facets. In this embodiment, a 4-mirror gonio lens is chosen because it gives the best light coverage and requires the least amount of rotation to obtain complete coverage. FIG. 12 illustrates a 4-mirror gonio lens, each mirror being at 62°. Four 62° millions give a 360° view, thereby a 360° projection of the anterior chamber angle with only a slight lens rotation. Such a gonio lens is available from Opt Electronics S. A. Medical Division Model 04GFA, or a Thorpe 4-mirror gonio laser lens Model OT4Mga. Other four mirror configurations can be used, such as the Ritch Trabeculopasty laser Lens Model ORTA, as well as single mirror or two mirror lenses. Examples are the Magic View Gonio laser lens Model OmVGL and the Single Mirror Gonio laser lens Model OSNGA, both having a single 62° mirror, and the two mirror gonio laser lens, Model 02MA having two opposing 62° mirrors. The gonio lens allows uniform rays from the irradiation source to get under the iris of the eye to the edges of the light adjustable lens, enabling total locking of the lens.

In General

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and/or steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. In a method for modifying the refractive power of a light adjustable lens in an optical system, with lens modifying radiation, the improvement comprising:

measuring at least one aberration in the system containing the lens;

aligning a source of the modifying radiation so as to impinge the radiation onto the lens in a pattern that corresponds to the correction of the at least one aberration; and controlling the quantity of the impinging radiation whereby to correct the at least one aberration;

wherein the impinging radiation is ultraviolet light obtained from a source thereof; and the ultraviolet light has a wavelength in the range of 350 to 380 nm and is applied at a power of 2.5 to 3.5 mW.

2. The method of claim 1 in which the quantity of the impinging radiation is controlled by controlling the intensity and duration of the irradiation.

3. The method of claim 1 in which the pattern of the impinging radiation is controlled and monitored while the lens is irradiated.

4. The method of claim 1 including the step of irradiating the entire lens to lock in the modified refractive power.

5. The method of claim 4 in which the modified refractive power of the light adjustable lens is locked in by non-patterned radiation.

6. The method of claim 1 in which the optical system comprises the light adjustable lens as an intraocular lens implanted in an eye.

7. The method of claim 1 in which the optical system comprises the light adjustable lens as a customized contact lens to be used in ophthalmic systems or ophthalmic applications.

8. The method of claim 1 in which the optical system possesses at least one light adjustable refraction element that can be used to null the aberrations present in the system to improve image quality.

9. The method of claim 1 in which the ultraviolet light source comprises a plurality light emitting diodes whose outputs are directed onto the receiving end of a light pipe that directs the ultraviolet light onto the lens.

10. The method of claim 9 in which the light pipe is an optical fiber.

11. The method of claim 1 in which the ultraviolet light source comprises the output of a pulsed ultraviolet light laser.

12. The method of claim 1 in which the ultraviolet light is from a pulsed ultraviolet light laser.

13. The method of claim 1 in which the ultraviolet light has a wavelength in the range of 350 to 380 nm and is applied at an intensity of 9.75 to 12.25 $mW/cm^2$.

14. The method of claim 13 in which the radius (r) of the lens increases by the formula: $(1-r^2)/r^2$.

15. The method of claim 1 in which the ultraviolet light source generates continuous wave ultraviolet light.

16. The method of claim 15 in which the continuous wave ultraviolet light is obtained from an arc lamp.

17. The method of claim 15 in which the continuous wave ultraviolet light is obtained from a continuous wave light emitting diode.

18. The method of claim 15 in which the continuous wave ultraviolet light is obtained from a continuous wave laser.

19. The method of claim 18 in which an ultraviolet vertical-cavity surface-emitting laser array is used to generate the pattern and project it onto the surface of the light adjustable lens.

20. The method of claim 18 in which the pattern is obtained by projecting ultraviolet light through an apodizing filter having a predetermined intensity profile.

21. The method of claim 18 in which the pattern is obtained by reflecting ultraviolet light from a digital light processor.

22. The method of claim 18 in which the pattern is obtained by projecting ultraviolet light through a spatial light modulator.

23. The method of claim 22 in which the photo-feedback is obtained from a Shack Hartmann sensor.

24. The method of claim 18 in which the pattern is obtained by photo-feedback.

25. The method of claim 24 in which the non-patterned radiation has a "top hat" intensity profile.

26. The method of claim 24 in which the non-patterned radiation has an intensity profile that diminishes as the radius of the lens increases.

27. The method of claim 24 wherein the optical system comprises the light adjustable lens as an intraocular lens implanted in an eye in which the iris does not fully dilate, and wherein the non-patterned radiation is projected through a gonio lens.

* * * * *